United States Patent [19]

Nielsen

[11] Patent Number: 4,660,561
[45] Date of Patent: Apr. 28, 1987

[54] FIXTURE FOR SKIN TANNING BY SELECTIVE LIGHT SOURCE
[75] Inventor: Robert Nielsen, Sierra Madre, Calif.
[73] Assignee: Solana, Inc., Irwindale, Calif.
[21] Appl. No.: 665,113
[22] Filed: Oct. 26, 1984
[51] Int. Cl.[4] ............................................. A61N 5/06
[52] U.S. Cl. .................................... 128/376; 128/396; 248/325; 362/218; 362/230
[58] Field of Search ..................... 128/376, 395, 396; 248/325, 364; 297/391; 362/131, 250, 218, 220, 225, 373, 230

[56] References Cited

U.S. PATENT DOCUMENTS 4,124,249 11/1978 Abbeloos ............................ 297/391
4,241,891 12/1980 Rudolph ............................. 248/325
4,335,724 6/1982 Frei et al. ....................... 128/376 X

FOREIGN PATENT DOCUMENTS 2848234 9/1979 Fed. Rep. of Germany ...... 128/396
2831013 1/1980 Fed. Rep. of Germany ...... 128/395
3017355 11/1981 Fed. Rep. of Germany ...... 128/395
3044929 6/1982 Fed. Rep. of Germany ...... 128/396
3123378 1/1983 Fed. Rep. of Germany ...... 128/396

OTHER PUBLICATIONS

SunTana SunSystem brochure, 2 pages.
Super Tan brochure, 2 pages.

Primary Examiner—Anton O. Oechsle
Attorney, Agent, or Firm—Beehler, Pavitt, Siegemund, Jagger, Martella & Dawes

[57] ABSTRACT

A skin tanning fixture which may be in the form of a couch with an adjustable cover makes use of a battery of light emitting tubes on the lower side over which is a translucent body supporting sheet. A comparable battery of light emitting tubes are arcuately disposed beneath a reflector on the underside of the cover and also protected by a translucent sheet. There is a greater number of tubes used on the cover than on the lower side and tubes on both sides are arranged in a compact relationship sufficient to generate an energy density of ultraviolet A light rays sufficient to build up a tanning effect in the skin in substantially greater proportion than the proportionate increase in the amount of energy density present due to an increase in the number of tubes.

14 Claims, 16 Drawing Figures

FIXTURE FOR SKIN TANNING BY SELECTIVE LIGHT SOURCE

The invention here concerned is a skin tanning system of the type which makes use of ultraviolet light in those ranges useful for tanning and which are not otherwise harmful. More particularly the skin tanning system is embodied in a couch on which the subject can recline while virtually surrounded by ultraviolet light in the beneficial range for a limited period of time during each of successive treatments which may continue over a period of days, weeks, or even months.

Tanning systems making use of artificial light in one form or another have been in vogue for an appreciable length of time and have been especially popular during winter months when a natural tan cannot be readily acquired and particularly in those countries where the summer tanning season is relatively short. Although it has been possible by using such known systems to acquire a tan, it has not been without some limitations, chief among which is the likelihood of getting an overdose of ultraviolet rays, especially on sensitive skin, as the result of overexposure. Another shortcoming of available tanning systems is the inability to enjoy the tanning effect on any more than one portion of the skin at one time.

It is accordingly among the objects of the invention to provide a new and improved tanning system making use of tubes as a source of artificial sunlight of such character that ultraviolet light in only the U.V.A. range predominates and there is little likelihood of the skin of the subject being burned or being subjectd to an exposure which might have a drying or deteriorating effect upon the skin.

Another object of the invention is to provide a new and improved tanning system which makes use of predominantly ultraviolet light in the U.V.A. range in an arrangement such that virtually all sides of the body of the user are subjected simultaneously to the tanning effect.

Another object of the invention is to provide a new and improved tanning system making use of tubes emitting predominantly ultraviolet light in the U.V.A. range wherein the tubes are of uniform length and capacity but are arranged in a special fashion so that the distribution of the tanning effect on one side of the body may be quite different from the tanning effect on the other side of the body where that condition may be desirable.

Still another object of the invention is to provide a new and improved tanning system making use of artificial light wherein by an appropriate concentration of tubes as a source of light an appreciably accelerated tanning effect may be secured with only a modest increase in the energy density generated by a bank of tubes.

Still another object of the invention is to provide in a new and improved tanning system a fixture in the nature of a couch upon which the subject may recline, the couch being fitted with an adjustable canopy arranged in such fashion that electrical components needed for the proper functioning of electrically actuated source of tanning rays serve additionally as a means for counterbalancing the adjustment of the canopy so that the subject can very easily and readily readjust the canopy to his liking either manually or automatically whenever desirable.

Still further among the objects of the invention is to provide in a new and improved tanning system an article of furniture such as a couch upon which the subject may recline while the tanning effect proceeds, the couch being so fitted as to simultaneously envelope all sides of the subject, the fixture, however, being one of relatively inexpensive construction as compared to those heretofore resorted to but without sacrifice in the tanning effect obtainable in a safe and dependable manner.

With these and other objects in view, the invention consists of the construction, arrangement, and combination of the various parts of the device serving as an example only of one or more embodiments of the invention, whereby the objects contemplated are attained, as hereinafter disclosed in the specification and drawings, and pointed out in the appended claims.

In an embodiment of the invention chosen for the purpose of illustration, there is shown a fixture indicated generally by the reference character 10 consisting principally of a couch or bed 11 in an appropriate framework surmounted by a canopy 12 in its frame. The canopy is supported by a column 13 at the rear of the couch on which is tiltably mounted an intermediate assembly 14, the free end of which carries the canopy.

Figure 1:
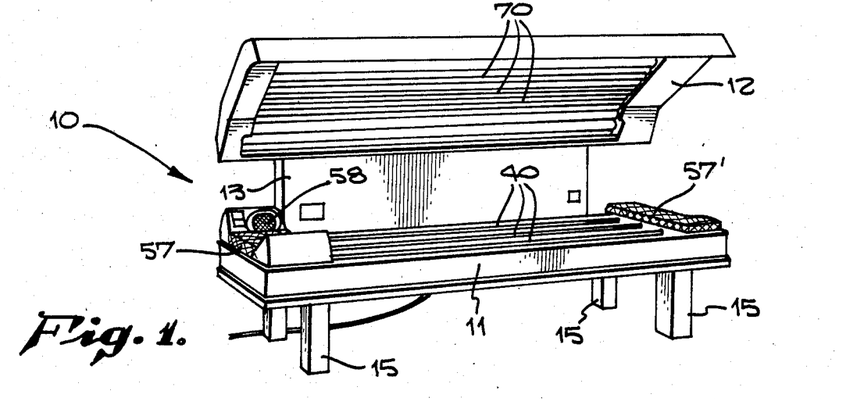
FIG. 1 is a front perspective view of a typical fixture in which the tanning system can operate.
Figure 2:
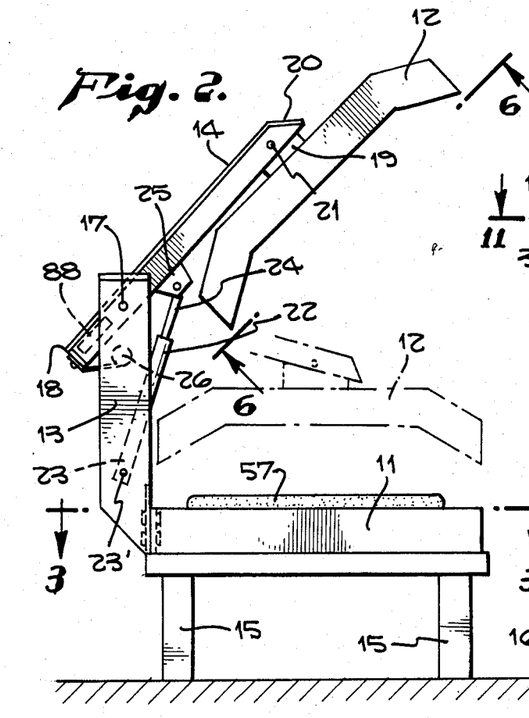
FIG. 2 is an end elevational view of the fixture of FIG. 1.

In the embodiment of FIG. 1, the couch is carried by four legs 15 at a desired distance above a supporting surface 16. The column 13, extending upwardly from the rear of the couch, carries the intermediate assembly 14 at a pivot point 17 which is located inwardly from a captive end 18 of the intermediate portion. A bracket 19 on the canopy 12 is tiltably attached to a free end 20 of the intermediate portion 14 at a pivot point 21.

As an aid in stabilizing movment of the canopy 12, there is provided a dampener 22 attached at a lower end 23 to a lower portion of one of two box extrusions 28 at ends of the column 13 at a pivot point 23' and attached at an upper end 24 to a bracket 25 on the intermediate assembly 14 between the free end 20 and the pivot point 17. To further control manipulation of the canopy 12, there is provided a geared motor 26, a shaft 27 of which is supported in the vertical box extrusion 28 in a bushing 27'. The geared motor 26 drives a spool 29 around which is secured a flat webbing 30, the other end of which is attached to the intermediate assembly 14 at its free end 18.

In addition to serving as a support for the canopy, the structure of the column 13 in general is such that it provides a shelf 36 in a chamber 31 for the mounting of sundry components 32, 33, 34, 35, etc., useful in operation of the tanning system and the movable physical items such as the canopy 12.

Figure 4:
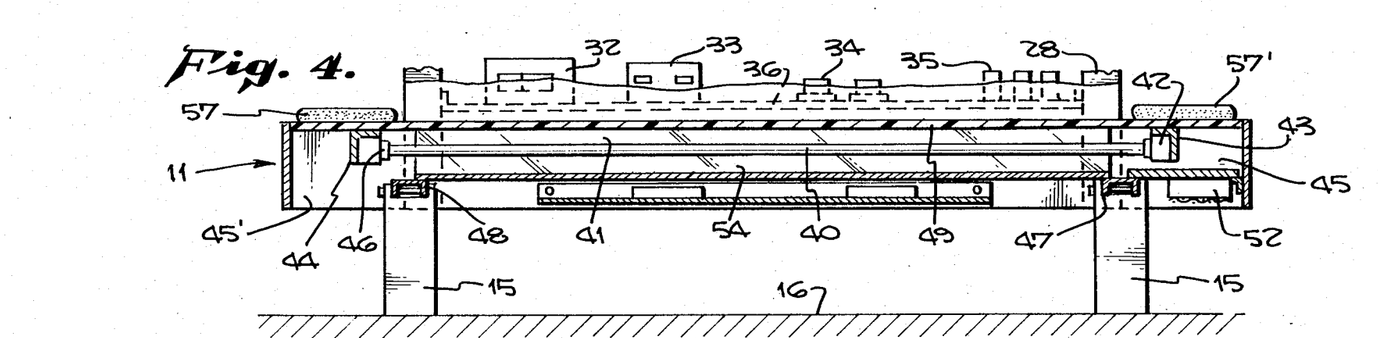
FIG. 4 is a longitudinal sectional view on the line 4—4 of FIG. 3.

Mounted in the couch 11 are lamps in the form of tubes 40 for the tanning system. In the chosen embodiment there are twelve of the tubes 40 comprising a bank of tubes in side by side contiguous relationship within a space 41 of that portion of the couch which may be considered as a tube housing. Lamp sockets 42 at the right end of the couch, as viewed in FIG. 4, are compactly mounted side by side on an appropriate mounting strip 43. Being spaced from the end of the couch, the strip allows for an auxiliary space 45. At the opposite or left-hand end, as viewed in FIG. 4, is a mounting strip 44 spaced from the adjacent end of the couch leaving an auxiliary space 45'. Strip 44 provides an appropriate mounting for the lamp sockets 46 in their closely compacted relationship.

Figure 3:
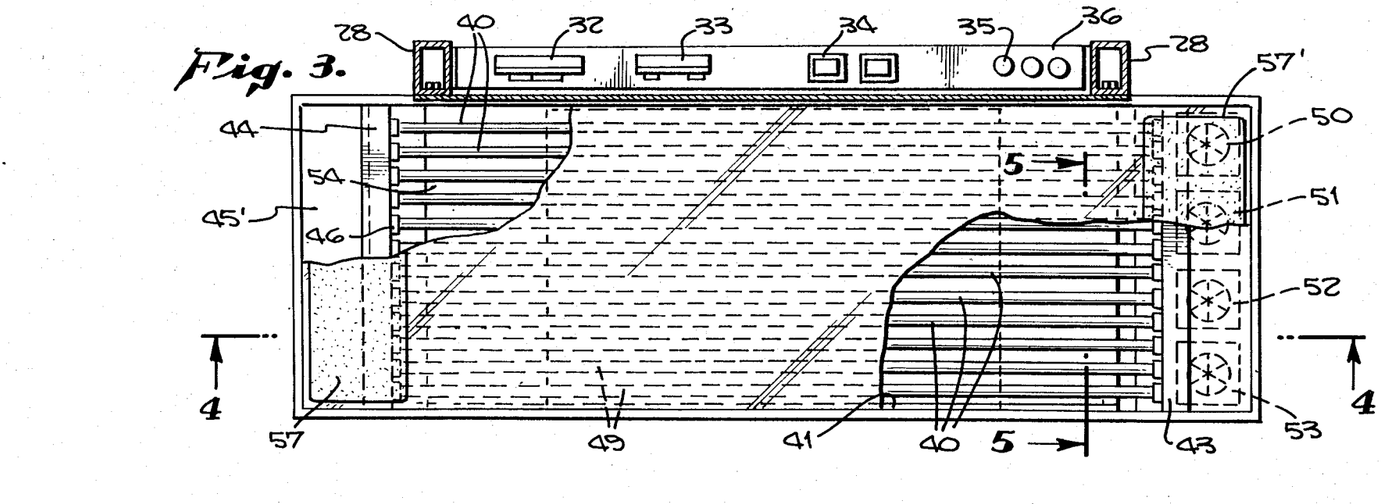
FIG. 3 is a horizontal partially sectional view on the line 3—3 of FIG. 2.

A reflector 46 extends throughout the full length of the tubes 40 and is designed to be supported upon struts 47 and 48 of conventional construction at a location spaced from the bank of tubes 40. Extending completely over the entire bank of tubes is a lamp cover 49 serving also as a user lay-on surface. The lamp cover 49 is translucent and preferably made of an appropriate synthetic plastic resin material. The space 41 between the lamp cover 49 and the reflector 46 is vented at the right-hand, end, as viewed in FIG. 3, by four muffin fans 50, 51, 52 and 53. The fans draw off heat generated by operation of the bank of tubes 40 at a rate which permits the space 41 to remain sufficiently warm to help keep the space above the lamp cover as well as the lamp cover itself sufficiently warm to satisfy the tanning process.

Providing additional support for the lamp cover 49 are folds 54 in the reflector 46 intermediate opposite side edges, the folds terminating in ridges 55 at a location serving to engage the underside of the lamp cover 49 and providing support at corresponding locations throughout the length of the lamp cover. Edges of the smaller side sections of the reflector may be folded over adjacent edges of the larger interior section of the reflector to provide a neater, stronger, support. The folds 54 in company with folded edges 56 serve also to separate the bank of tubes 40 into compartments, narrower compartments at the side edges housing three tubes in contiguous relationship, and a wider central compartment housing six tubes, likewise in a relationship as close as structurally achievable.

Pillows are provided for the user above the lamp cover 49, there being a pillow 57' for the feet and a pillow 57 for the head. The pillows 57' and 57 extend over the auxiliary spaces 45 and 45' and the pillows at the head end may, if preferred, be provided with amenities such, for example, as stereo sound speakers 58 mounted in a conventional manner at the sides of the pillow for diversion of the user while being subject to the tanning system.

For tanning the opposite side of the user's body to that resting upon the lamp cover 49 or lay-on surface, lamps in the form of tubes 70 are provided in the canopy 12.

Figures 6, 7, 8:
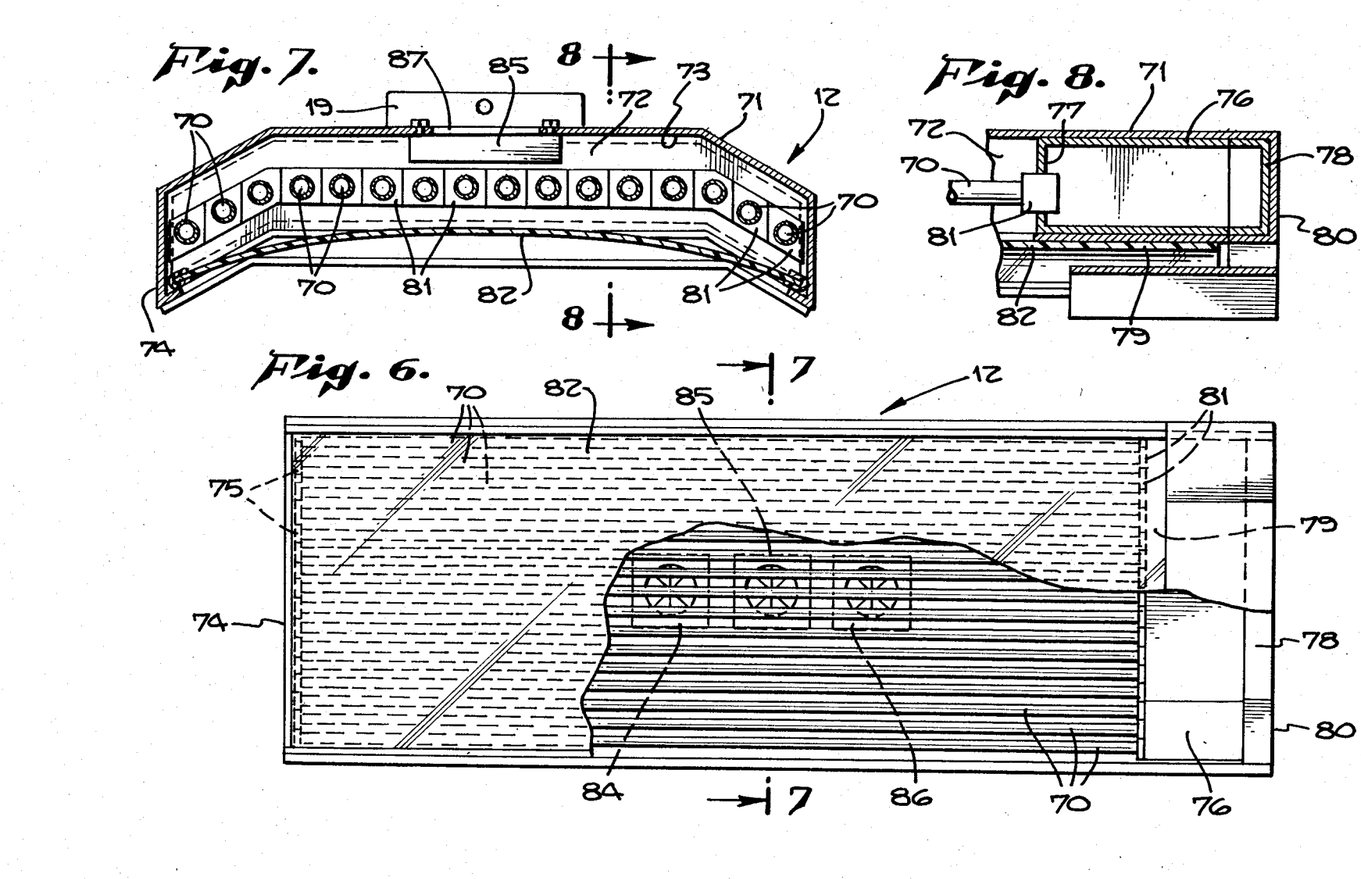
FIG. 6 is a longitudinal view partially broken away taken on the line 6—6 of FIG. 2.
FIG. 7 is a cross-sectional view on the line 7—7 of FIG. 6.
FIG. 8 is a fragmentary cross-sectional view on the line 8—8 of FIG. 7.
Figure 9:
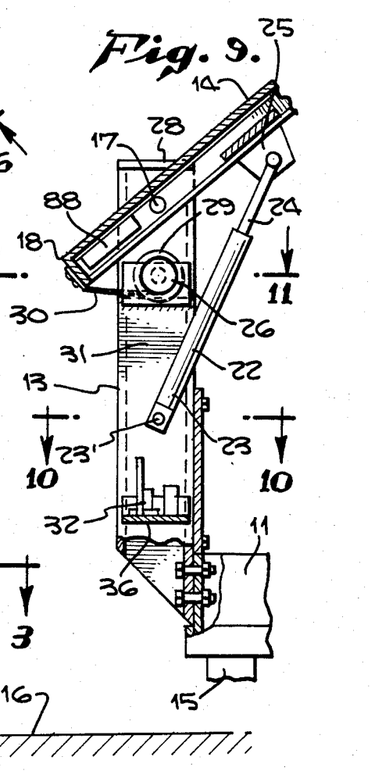
FIG. 9 is a vertical fragmentary sectional view of the rear portion of the fixture as shown in FIG. 2.

What has been heretofore designated as a canopy is embodied in a frame 71 of conventional sheet material housing the tubes 70, numbering 16 in the chosen embodiment, within a space 72. At the rear of the space 72 the interior surface 73 of the frame 71 is polished and serves as a reflecting surface. On the opposite face of the frame is an arcuate translucent lamp cover 82. Covering the space 72 at the left end of the frame, as viewed in FIGS. 6 and 7, is a panel bracket 74 which provides a means for mounting lamp sockets 75. At the opposite end is a bracket 76, an inner side wall 77 of which is spaced from an outer side wall 78, whereby to provide an auxiliary space 79 on the inner side of an end panel 80. Lamp sockets 81 are mounted on the side wall 77.

It is of consequence to note that the frame 71 has a somewhat arcuate shape in cross-section in order to have the bank of tubes 70 likewise in a somewhat arcuate shape. The outermost three tubes on each side are displaced from the plane of the intermediate tubes but the tubes remain contiguously spaced in side by side relationship to provide a condition of optimum energy density. It is of consequence to note that the lamp sockets are stacked in contiguous side by side relationship at both ends, as close a structurally feasible, so that tubes 70 comprising the bank are comparably close together to achieve the maximum available energy density level at the source, namely, an energy density over a threshold for marked increase in the ultimate tanning effect produced by the system. The arrangement of tubes in close side by side proximity, as made reference to with respect to the canopy, is also likewise the arrangement with respect to the tubes as mounted in the couch, except for the space occupied by the folds of the reflector near the side edges. The marked increase in the tanning effect is for this reason made possible while continuing use of tubes of the same character, namely, those which dispense ultraviolet light in the proportion UVA 99% and UVB 0.7% to 1%.

It should additionally be noted that the auxiliary space 79 in the frame 71 is at the end opposite the head end where there is less need for application of the tanning process. The auxiliary spaces 45 and 45' provided in the couch 11, where tubes do not extend, are covered by the pillows. The staggered relationship of upper versus lower tubes affords a more effective use of the high level energy density in that a user reclining on the back side of the body on the couch with a pillow 57 at the head end, as shown, needs little or no tanning effect at the back of the neck where growth of hair ordinarily blocks tanning. There is, by contrast, a full tanning effect in the area of the face derived from full exposure to the bank of tubes 70 at the left end of the canopy 12.

For venting the space 72 within th frame 71, three fans 84, 85 and 86 are mounted on the top face of the frame 71 so as to draw through appropriate openings 87 from the space. Conventional inlet cooling means (not shown) may be provided in the frame 71 for the space 72. In practice the skin of the user needs to be warm in order to activate the tanning effect of the system. Since in use the canopy is lowered over the couch to a position somewhat encompassing the user's body, some of the heat generated by the banks of tubes needs to be dispelled from both top and bottom in order that the user may remain comfortable while being warm and subject to the tanning process.

To further help the user adjust the system to a comfortable level, the canopy is carefully counterbalanced. The user can therefore readily lift or adjust the level of the canopy above the body, either physically by no more than finger pressure or, if preferred, by appropriate power operated means. Counterbalancing is enhanced by use of ballast components 88 for the upper bank of tubes 70 as a counterweight on the opposite side of the pivot point 17 from the free end 20 on which the canopy 12 is slung.

Figures 5, 10, 11, 12, 13:
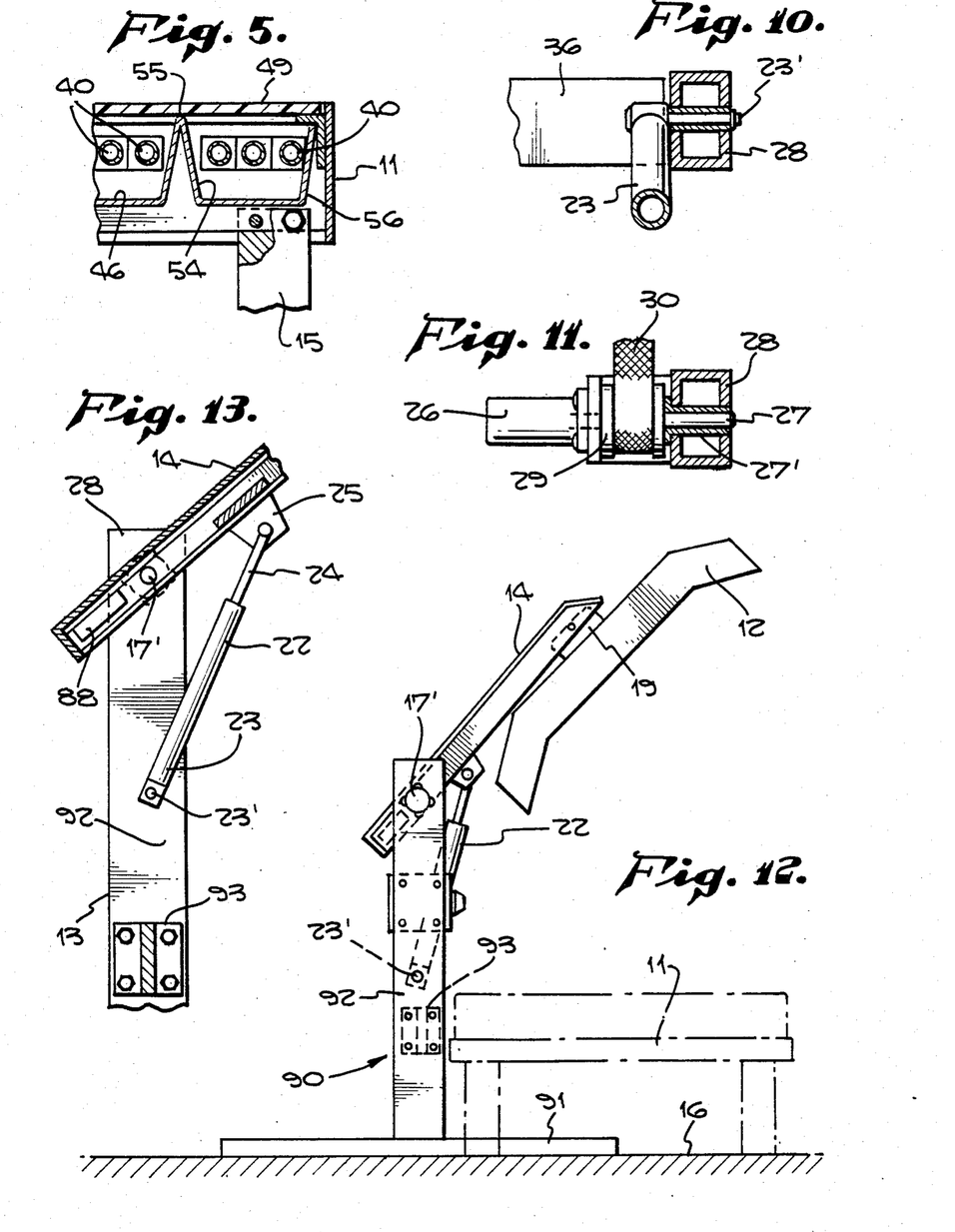
FIG. 5 is a fragmentary cross-sectional view on the line 5—5 of FIG. 3.
FIG. 10 is a fragmentary sectional view on the line 10—10 of FIG. 9.
FIG. 11 is a cross-sectional view on the line 11—11 of FIG. 9.
FIG. 12 is an end elevational view of a modified form of the fixture.
FIG. 13 is a fragmentary vertical sectional view of the rear portion of the form of FIG. 12.

In a modified form of the invention of FIGS. 12 and 13, there is provided a canopy support assembly 90, separate and apart from the couch 11'. In this arrangement a relatively broad base 91 may be employed so as to have a portion slide under the couch 11' in order to have posts 92 moved to positions along one side of the couch without need for being physically attached to the couch. The posts 92 on opposite ends of the canopy support assembly are connected together by a beam 93 to provide support for opposite ends of the intermediate assembly at pivot points 17'. Components 32, etc., previously made reference to, are adapted to be mounted, if preferred, on an appropriate shelf of conventional construction, either attached to one or another of the posts 92 or supported by the beam 93.

Figure 14:
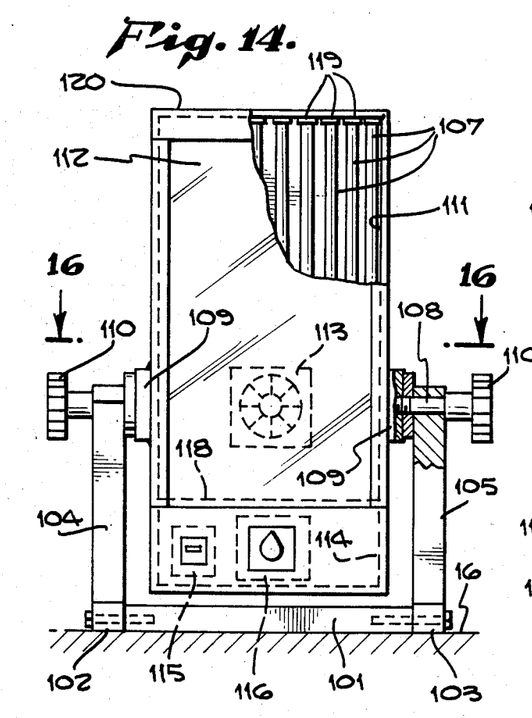
FIG. 14 is a front elevational view partially broken away of still another modified form of the device.
Figure 15:
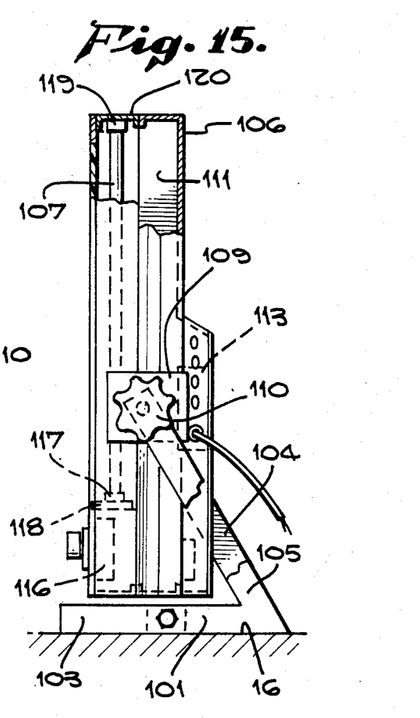
FIG. 15 is a side elevational view partly broken away of the device of FIG. 14.
Figure 16:
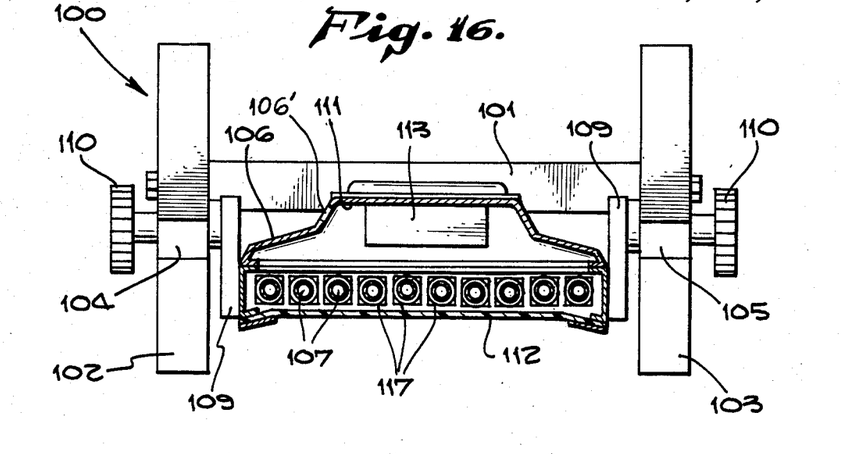
FIG. 16 is a cross-sectional view on the line 16—16 of FIG. 14.

In a more simplified version of the device, as shown in FIGS. 14, 15 and 16, useful, for example, in applying the tanning process to just the neck and face, there is provided a support assembly 100 embodied in a transverse base 101, at opposite ends of which are left and right-hand feet 102 and 103. On the feet, respectively, are upright posts 104 and 105. Pivotally mounted at the tops of the posts 104 and 105 is a frame 106 for housing a bank of vertically mounted tubes 107. Shafts 108 extending outwardly from bushing 109 on opposite sides of the frame serve to tiltably support the frame at the tops of the posts 104 and 105. Handles 110 are provided for tightening the frame at a selected angle of tilt.

The somewhat dished shape of the frame 106 of conventional sheet material, as shown in FIG. 16, has a polished reflecting surface on the interior face. Positioned as shown, the frame provides a ventilated space 111 rearwardly of the bank of tubes 107. A translucent lamp cover 112 extends over the entire bank of tubes and serves to enclose the forward portion of the space 111. A fan 113 mounted on the rear face of the frame 106 substantially at the axis of rotation of the shafts 108 serves to exhaust heat generated by the tubes 107 from the space 111. By having the frame 106 extend for a distance vertically longer than the lengths of the tubes 107, there is provided a chamber 114 within which may be mounted appropriate components 115 and 116 for operation of the tubes under circumstances where the weight of the components is helpful in counterbalancing that portion of the assembly located on the upper side of the shafts 108. Lamp sockets 117 are mounted on a wall 118 enclosing the upper side of the chamber 114, lamp sockets 119 at the opposite end being carried by an appropriate transverse end wall 120 of the frame. There is a hole 106' shown in the frame 106 which exemplifies a conventional means for admitting outside air to the space 111 vented by the fan 113.

As in other forms of the invention, the lamp sockets 117, 119 are mounted in contiguous relationship to have tubes 107 of the bank in close side by side relationship. As a consequence, here also there is what may be termed a blanket of energy created by the tubes which is at a substantially maximum level over the threshold of energy where the rate and effectiveness of the tanning operation is enhanced at a substantially greater proportion than the added energy needed to reach the threshold.

While a particular embodiment of the present invention has been shown and described, it will be obvious to those skilled in the art that changes and modifications may be made without departing from the invention in its broader aspects and, therefore, the aims of its appended claims are to cover all such changes and modifications as fall within the true spirit and scope of this invention.

Having described the invention, what is claimed as new in support of Letters Patent is as follows:

1. A fixture for skin tanning of a user by a selective light source of substantially optimum energy density comprising a supporting structure for engagement with a supporting surface, a frame for containment of said light source, an adjustable connection between said supporting structure and said frame comprising means enabling simultaneous adjustment of vertical location and tilt of said frame relative to the skin surface of a user, said light source comprising a multiple number of light emitting tubes forming a bank of tubes, said bank having when energized a light emitting capability of about 99% UVA and from about 0.7% to 1% UVB, said frame comprising a tube housing having opposite ends spaced from each other at a distance in excess of the length of a tube and a rear wall, a set of tube holders at each end in substantially contiguous relationship for reception of said tubes in relatively snug juxtaposition, reflecting means facing inwardly relative to said rear wall and a transparent sheet of synthetic plastic resin material extending over the forward side of said bank of tubes, there being a space between said tubes and said rear wall and vent means in communication between said space and the exterior, a second bank of tubes, the second bank of tubes including a substantially flat sheet member in substantially horizontal position for supporting the body of the user and adapted to engage one side of said body, the other of said banks including a corresponding sheet member adapted to be moved into a substantially horizontal position at selected levels for tanning the other side of the body, there being a greater number of tube mountings and tubes in said other of said banks, said other of said banks having a substantially flat intermediate section, a set of tube mountings and tubes adjacent opposite side edges of said other of said banks having a width less than the width of said intermediate section and being in planes obliquely disposed relative to the plane of said intermediate section for tanning side portions of the user's body.

2. A fixture for skin tanning as in claim 1 wherein there is a relatively stationary frame for said one of said banks, said other of said banks being mounted in the first identified frame, said frames each having a length in excess of the length of said tubes, said tubes of one of said banks being mounted more nearly adjacent one end of the corresponding frame than the other end whereby to provide an auxiliary space intermediate tube ends and the adjacent end of the respective frame, the location of the auxiliary space for one of said banks being offset with respect to the auxiliary space for the other of said banks.

3. A fixture for skin tanning as in claim 2 wherein there is a reflector for one of said banks having folds therein extending in a direction parallel to said tubes forming a plurality of recesses and a multiple number of said tubes in each recess, said folds being in supporting engagement between the frame and the respective sheet.

4. A fixture for skin tanning as in claim 2 wherein said reflecting means resides between the relatively movable frame and the tubes at a location spaced from the bank of tubes of said frame whereby to form a cooling compartment, said vent means for said space being a mechanically actuated means.

5. A fixture for skin tanning as in claim 4 wherein there is a reflector for said one of said banks having folds extending in a direction parallel to said tubes and in supporting relationship with the corresponding sheet, means forming a compartment on the side of the reflector proximate said tubes in communication with the corresponding auxiliary space and mechanically actuated vent means between said auxiliary space and ambient atmosphere.

6. A fixture for skin tanning as in claim 2 wherein there is a footing on said relatively stationary frame for engagement with a supporting surface, a base portion on said relatively movable frame for engagement with said supporting surface at a location adjacent said footing, an upright column on said base portion and a tiltable connection between said column and said relatively shiftable frame whereby to alter the position of said relatively shiftable frame with respect to said relatively stationary frame.

7. A fixture for skin tanning as in claim 6 wherein there is counterbalance means between the column and said relatively movable frame whereby to absorb a portion of weight of said relatively movable frame during movement.

8. A fixture for skin tanning of a user by a selective light source of substantially optimum energy density comprising a supporting structure for engagement with a supporting surface, a frame for containment of said light source, an adjustable connection between said supporting structure and said frame whereby to adjust the location of said frame relative to the skin surface of a user, said light source comprising a multiple number of light emitting tubes forming a bank of tubes, said bank having when energized a light emitting capability of about 99% UVA and from about 0.7% to 1% UVB, said frame comprising a tube housing having opposite ends spaced from each other at a distance in excess of the length of a tube and a rear wall, a set of tube holders at each end in substantially contiguous relationship for reception of said tubes in relatively snug juxtaposition, relfecting means facing inwardly relative to said rear wall and a transparent sheet of synthetic plastic resin material extending over the forward side of said bank of tubes, there being a vent space between said tubes and said rear wall and vent means for said space, a second bank of tubes the second bank of tubes including a substantially flat sheet member in substantially horizontal position for supporting the body of the user and adapted to engage one side of said body, the other of said banks including a corresponding sheet member adapted to be moved into a substantially horizontal position for tanning the other side of the body, there being a greater number of tube mountings and tubes in said other of said banks, said other of said banks having a substantially flat intermediate section, a set of tube mountings and tubes adjacent opposite side edges of said other of said banks having a width less than the width of said intermediate section and being in planes obliquely disposed relative to the plane of said intermediate section for tanning side portions of the user's body, a relatively stationary frame for said second of said banks, said frames each having a length in excess of the length of said tubes, said tubes of one of said banks being mounted more nearly adjacent one end of the corresponding frame than the other end whereby to provide an auxiliary space intermediate tube ends and the adjacent end of the respective frame, the location of the auxiliary space for one of said banks being offset with respect to the auxiliary space for the other of said banks, there being twelve tubes in said second of said banks, a reflector for said second of said banks having folds therein exteding in a direction parallel to said tubes forming a central recess for a multiple number of said tubes and edge recesses for tubes on opposite sides of said central recess each having a breadth less than the breadth of said central recess, said folds being in supporting engagement between the frame and the respective sheet.

9. A fixture for skin tanning as in claim 8 wherein there are six tubes in said central recess and three tubes in each of said edge recesses.

10. A fixture for skin tanning of a user by a selective light source of substantially optimum energy density comprising a supporting structure for engagement with a supporting surface, a frame, an adjustable connection between said supporting structure and said frame whereby to adjust the location of said frame relative to the skin surface of a user, said light source comprising a multiple number of light emitting tubes forming a bank of tubes, said bank having when energized a light emitting capability of about 99% UVA and from about 0.7% to 1% UVB, said frame including a tube housing having opposite ends spaced from each other at a distance in excess of the length of a tube and a rear wall, a set of tube holders at each end in substantially contiguous relationship for reception of said tubes in relatively snug juxtaposition, a reflector adjacent said rear wall and a transparent sheet of synthetic plastic resin material extending over the forward side of said bank of tubes, there being a vent space between said tubes and said rear wall and vent means for said space, a second bank of tubes, the second bank of tubes including a substantially flat sheet member in substantially horizontal position for supporting the body of the user and adapted to engage one side of said body, the other of said banks including a corresponding sheet member adapted to be moved into a substantially horizontal position for tanning the other side of the body, there being a greater number of tube mountings and tubes in said other of said banks, said other of said banks having a substantially flat intermediate section, a set of tube mountings and tubes adjacent opposite side edges of said other of said banks having a width less than the width of said intermediate section and being in planes obliquely disposed relative to the plane of said intermediate section for tanning side portions of the user's body, a relatively stationary frame for said second of said banks said frames each having a length in excess of the length of said tubes, said tubes of one of said banks being mounted more nearly adjacent one end of the corresponding frame than the other end whereby to provide an auxiliary space intermediate tube ends and the adjacent end of the respective frame, the location of the auxiliary space for one of said banks being offset with respect to the auxiliary space for the other of said banks, said relatively shiftable frame comprising a vertically disposed column, a hood for reception of said other bank of tubes and an intermediate section having a free end and a captive end, said hood being pivotally slung at the free end of said intermediate section, the captive end of said intermediate section having a pivotal attachment between the column and the intermediate section at a location spaced from the endmost portion of said captive end whereby to provide a counterbalance portion and electrical ballast means for said tubes mounted in said counterbalance portion, thereby to augment the counterbalance effect.

11. A fixture for skin tanning of a user by a selective light source of substantially optimum energy density comprising a supporting structure for engagement with a supporting surface, a frame for containment of said light source, an adjustable connection between said supporting structure and said frame whereby to adjust the location of said frame relative to the skin surface of a user, said light source comprising a multiple number of light emitting tubes forming a bank of tubes, said bank having when energized a light emitting capability of about 99% UVA and from about 0.7% to 1% UVB, said frame comprising a tube housing having opposite ends spaced from each other at a distance in excess of the length of a tube and a rear wall, a set of tube holders at each end in substantially contiguous relationship for reception of said tubes in relatively snug juxtaposition, reflecting means facing inwardly relative to said rear wall and a transparent sheet of synthetic plastic resin material extending over the forward side of said bank of tubes, there being a vent space between said tubes and said rear wall and vent means for said space, a second bank of tubes, the second bank of tubes including a substantially flat sheet member in substantially horizontal positon for supporting the body of the user and adapted to engage one side of said body, the other of said banks including a corresponding sheet member adapted to be moved into a substantially horizontal position for tanning the other side of the body, there being a greater number of tube mountings and tubes in said other of said banks, said other of said banks having a substantially flat intermediate section, a set of tube mountings and tubes adjacent opposite side edges of said other of said banks having a width less than the width of said intermediate section and being in planes obliquely disposed relative to the plane of said intermediate section for tanning side portions of the user's body, a relatively stationary frame for said one of said banks, said frames each having a length in excess of the length of said tubes, said tubes of one of said banks being mounted more nearly adjacent one end of the corresponding frame than the other end whereby to provide an auxiliary space intermediate tube ends and the adjacent end of the respective frame, the location of the auxiliary space for one of said banks being offset with respect to the auxiliary space for the other of said banks, said relatively shiftable frame comprising a vertically disposed column, a hood for reception of said other bank of tubes and an intermediate section having a free end and a captive end, a pivot connection between said hood and the free end of said intermediate section, the captive end of said intermediate section having a pivot connection to the column.

12. A fixture for skin tanning as in claim 11 wherein there is a dampener having an operative engagement with said intermediate section at a location between said pivot connections and the column.

13. A fixture for skin tanning of a user by a selective light source of substantially optimum energy density comprising a supporting structure for engagement with a supporting surface, a frame for containment of said light source, an adjustable connection between said supporting structure and said frame whereby to adjust the location of said frame relative to the skin surface of a user, said light source comprising a multiple number of light emitting tubes formning a bank of tubes, said bank having when energized a light emitting capabilty of about 99% UVA and from about 0.7% to 1% UVB, said frame comprising a tube housing having opposite ends spaced from each other at a distance in excess of the length of a tube and a rear wall, a set of tube holders at each end in substantially contiguous relationship for reception of said tubes in relatively snug juxtaposition, reflecting means facing inwardly relative to said rear wall and a transparent sheet of synthetic plastic resin material extending over the forward side of said bank of tubes, there being a vent space between said tubes and said rear wall and vent means for said space, a second bank of tubes, the second bank of tubes including a substantially flat sheet member in substantially horizontal position for supporting the body of the user and adapted to engage one side of said body, the other of said banks including a corresponding sheet member adapted to be moved into a substantially horizontal position for tanning the other side of the body, there being a greater number of tube mountings and tubes in said other of said banks, said other of said banks having a substantially flat intermediate section, a set of tube mountings and tubes adjacent opposite side edges of said other of said banks having a width less than the width of said intermediate section and being in planes obliquely disposed relative to the plane of said intermediate section for tanning side portions of the user's body, a relatively stationary frame for said one of said banks, said frames each having a length in excess of the length of said tubes, said tubes of one of said banks being mounted more nearly adjacent one end of the corresponding frame than the other end whereby to provide an auxiliary space intermediate tube ends and the adjacent end of the respective frame, the location of the auxiliary space for one of said banks being offset with respect to the auxiliary space for the other of said banks, said relatively shiftable frame comprising a vertically disposed colunm, a hood for reception of said other bank of tubes and an intermediate section having a free end and a captive end, said hood being attached to said intermediate section adjacent the free end, the captive end of said intermediate section having a pivotal attachment between the column and the intermediate section at a location spaced from the endmost portion of said captive end whereby to provide a counterbalance portion for reception of counterbalance means, thereby to augment the counterbalance effect.

14. A fixture for skin tanning as in claim 13 wherein said counterbalance means comprises a flexible connection between the column and the captive end of said intermediate section and motor means in operative relationship with said flexible connection whereby to effect withdrawal and release of said captive end at said flexible connection.

* * * * *